(12) United States Patent
Beaupre

(10) Patent No.: US 10,874,417 B2
(45) Date of Patent: Dec. 29, 2020

(54) DOUBLE HOOK ULTRASONIC SURGICAL BLADE

(71) Applicant: Jean Beaupre, Alexandria, KY (US)

(72) Inventor: Jean Beaupre, Alexandria, KY (US)

(73) Assignee: REACH SURGICAL, INC., Tianjin (CN)

( * ) Notice: Subject to any disclaimer, the term of this patent is extended or adjusted under 35 U.S.C. 154(b) by 209 days.

(21) Appl. No.: 15/751,581

(22) PCT Filed: Aug. 11, 2016

(86) PCT No.: PCT/US2016/046626
§ 371 (c)(1),
(2) Date: Feb. 9, 2018

(87) PCT Pub. No.: WO2017/027745
PCT Pub. Date: Feb. 16, 2017

(65) Prior Publication Data
US 2018/0235650 A1   Aug. 23, 2018

Related U.S. Application Data

(60) Provisional application No. 62/203,694, filed on Aug. 11, 2015.

(51) Int. Cl.
*A61B 17/32* (2006.01)
*B26D 7/08* (2006.01)

(52) U.S. Cl.
CPC .............. *A61B 17/320092* (2013.01); *A61B 17/320068* (2013.01); *B26D 7/08* (2013.01);
(Continued)

(58) Field of Classification Search
CPC ............ A61B 17/32; A61B 17/320068; A61B 17/320092; A61B 2017/320094; A61B 2017/320074; A61B 2017/320072
See application file for complete search history.

(56) References Cited

U.S. PATENT DOCUMENTS 2,874,470 A   5/1954   Richards
3,844,272 A   10/1974  Banko
(Continued)

FOREIGN PATENT DOCUMENTS

GB   830142 A    3/1960
GB   2365775 A   2/2002
(Continued)

OTHER PUBLICATIONS

Supplementary European Search Report from corresponding European Application No. 16835941 dated Jun. 26, 2018.
(Continued)

*Primary Examiner* — Vi X Nguyen
(74) *Attorney, Agent, or Firm* — Porter Wright Morris & Arthur LLP

(57) ABSTRACT

An ultrasonic surgical device including an elongate waveguide having a longitudinal axis an a distal end, and a blade extending away from the distal end of the waveguide, the blade including a curved portion that includes first and second opposed faces extending lengthwise along at least a portion of the length of the blade. Each of the first and second faces has a width that extends perpendicular to the longitudinal axis of the waveguide and a length that extends orthogonal to the width. A pair of hook portions are located on opposite sides of the blade. A method of fabricating an ultrasonic surgical device is also provided.

26 Claims, 10 Drawing Sheets

(52) U.S. Cl.
CPC ............ *A61B 2017/320074* (2017.08); *A61B 2017/320075* (2017.08); *A61B 2017/320089* (2017.08); *A61B 2017/320093* (2017.08); *A61B 2017/320094* (2017.08); *A61B 2017/320095* (2017.08)

(56) References Cited

U.S. PATENT DOCUMENTS

| | | |
|---|---|---|
| 5,047,043 A | 9/1991 | Kubota et al. |
| 5,188,102 A | 2/1993 | Idemoto et al. |
| D339,419 S | 9/1993 | Hood et al. |
| D344,801 S | 3/1994 | Hughes et al. |
| 5,318,570 A | 6/1994 | Hood et al. |
| 5,322,055 A | 6/1994 | Davison et al. |
| 5,324,299 A | 6/1994 | Davison et al. |
| 5,346,502 A | 9/1994 | Estabrook et al. |
| 5,669,922 A | 9/1997 | Hood |
| 5,688,235 A | 11/1997 | Sakurai et al. |
| 5,746,756 A | 5/1998 | Bromfield et al. |
| 5,897,523 A | 4/1999 | Wright et al. |
| 5,906,628 A | 5/1999 | Miyawaki et al. |
| 5,935,144 A | 8/1999 | Estabrook |
| 6,206,844 B1 | 3/2001 | Reichel et al. |
| 6,254,622 B1 | 7/2001 | Hood |
| 6,283,981 B1 | 9/2001 | Beaupre |
| 6,309,400 B2 | 10/2001 | Beaupre |
| 6,325,811 B1 | 12/2001 | Messerly |
| 6,328,751 B1 | 12/2001 | Beaupre |
| 6,423,082 B1 | 7/2002 | Houser et al. |
| 6,660,017 B2 | 12/2003 | Beaupre |
| 6,752,815 B2 | 6/2004 | Beaupre |
| 6,761,698 B2 | 7/2004 | Shibata et al. |
| 7,479,148 B2 | 1/2009 | Beaupre |
| 7,799,045 B2 | 9/2010 | Masuda |
| 8,016,843 B2 | 9/2011 | Escaf |
| 8,057,498 B2 | 11/2011 | Robertson |
| 8,236,018 B2 | 8/2012 | Yoshimine et al. |
| 8,323,302 B2 | 12/2012 | Robertson et al. |
| 8,328,834 B2 | 12/2012 | Isaacs et al. |
| 8,348,967 B2 | 1/2013 | Stulen |
| 8,430,898 B2 | 4/2013 | Wiener et al. |
| 8,469,981 B2 | 6/2013 | Robertson et al. |
| 8,531,064 B2 | 9/2013 | Robertson et al. |
| 8,540,742 B2 | 9/2013 | Houser et al. |
| 8,814,870 B2 | 8/2014 | Paraschiv et al. |
| 8,911,460 B2 | 12/2014 | Neurohr et al. |
| 8,951,272 B2 | 2/2015 | Robertson et al. |
| 9,066,747 B2 | 6/2015 | Robertson |
| D749,730 S | 2/2016 | Dietz et al. |
| 2005/0273126 A1 | 12/2005 | Beaupre |
| 2008/0009848 A1 | 1/2008 | Paraschiv et al. |
| 2010/0057118 A1 | 3/2010 | Dietz et al. |
| 2012/0010537 A1 | 1/2012 | Young et al. |
| 2013/0116717 A1* | 5/2013 | Balek ............ A61B 17/320068 606/169 |
| 2013/0238004 A1 | 9/2013 | Young et al. |
| 2014/0107537 A1 | 4/2014 | Beaupre |
| 2014/0135804 A1* | 5/2014 | Weisenburgh, II .... A61B 17/29 606/169 |
| 2014/0163595 A1 | 6/2014 | Witt et al. |
| 2015/0164538 A1 | 6/2015 | Aldridge et al. |
| 2015/0282834 A1 | 10/2015 | Robertson |
| 2016/0242806 A1 | 8/2016 | Akagane |
| 2016/0367281 A1 | 12/2016 | Gee et al. |

FOREIGN PATENT DOCUMENTS

| | | |
|---|---|---|
| SU | 1388002 A1 | 4/1988 |
| WO | 01/24713 A1 | 4/2001 |
| WO | 2015/073428 A1 | 5/2015 |

OTHER PUBLICATIONS

Ultracision Incorporated, Harmonic Scalpel Operating Manual, pp. 1-53; Mar. 1995.

* cited by examiner

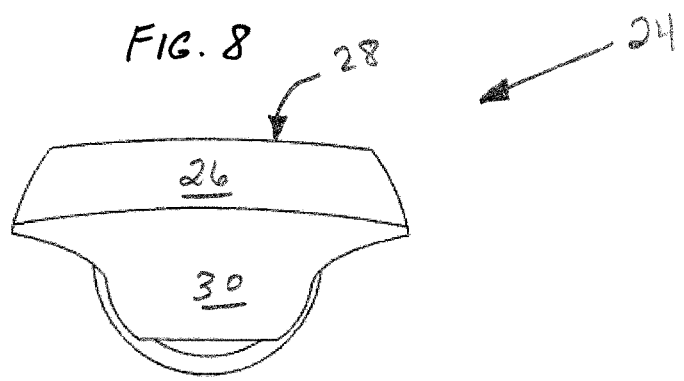
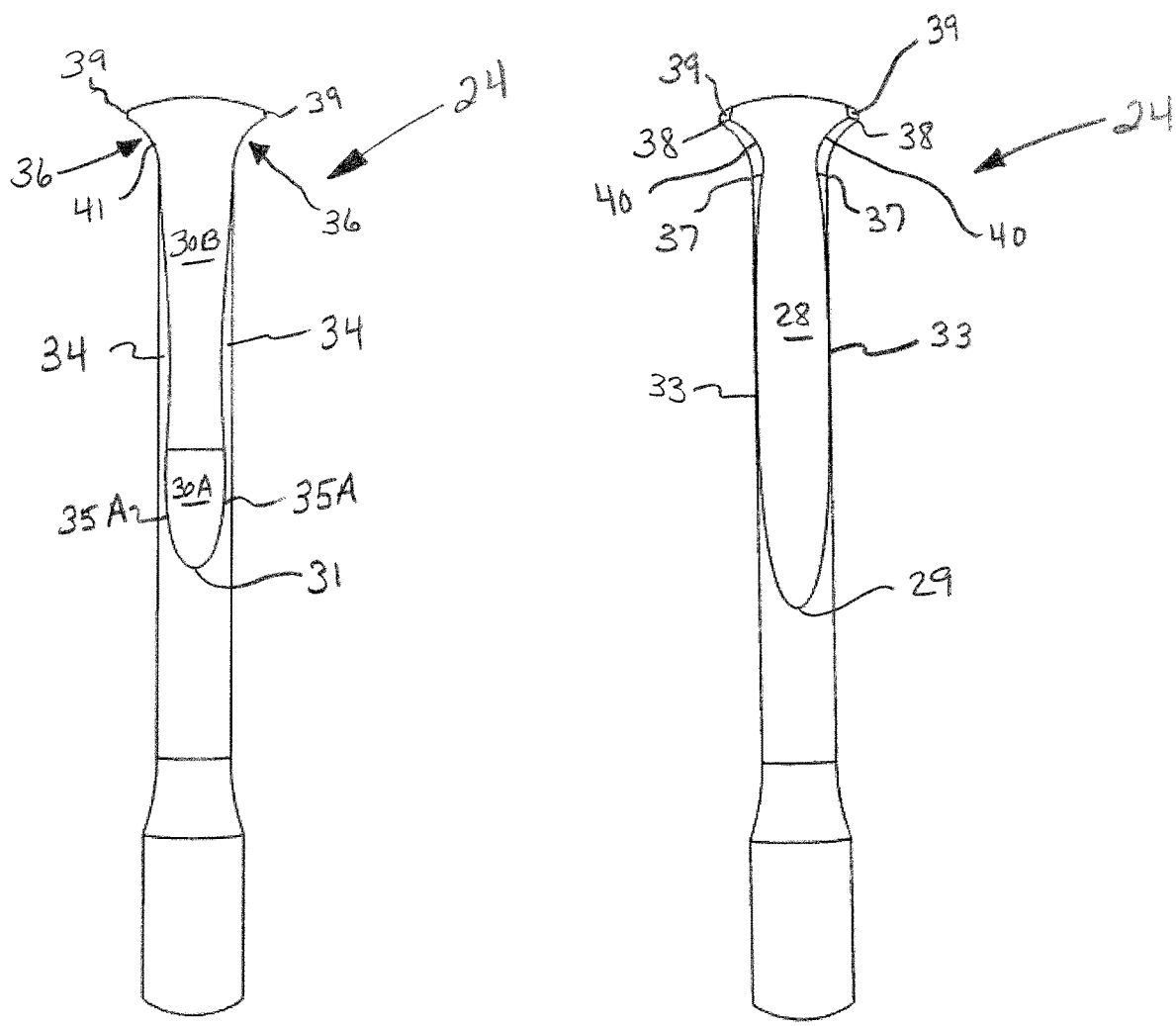

DOUBLE HOOK ULTRASONIC SURGICAL BLADE

CROSS REFERENCE TO RELATED APPLICATIONS

This application claims priority to U.S. Provisional Patent Application No. 62/203,694, filed on Aug. 11, 2015, entitled "Double Hook Ultrasonic Surgical Blade." The entire disclosure of the foregoing provisional patent application is incorporated by reference herein.

BACKGROUND

Ultrasonically driven surgical blades have been used for quite some time in the cutting, coagulation and/or dissection of tissue during various medical procedures. Compared to conventional static scalpels, for example, ultrasonically driven blades typically require less force for cutting tissue, and can also provide coagulation of blood vessels (particularly when the device includes a clamp member associated with the blade).

Ultrasonic surgical blades are usually provided at the end of an elongate waveguide, which in turn is operatively coupled to an ultrasonic transducer. The transducer, often provided as part of, or housed within, a handpiece, is adapted to convert electrical energy (typically supplied by an external generator) into vibrational motion, typically longitudinal vibrations, at an ultrasonic frequency. In many instances, the transducer includes a "Langevin stack" of piezoelectric disks for this purpose. The standing wave produced by the transducer is transmitted from the transducer to the waveguide, and propagates the length of the waveguide to the blade located at the distal end of the waveguide. As a result, the blade vibrates at an ultrasonic frequency.

When the ultrasonically vibrating blade is urged against tissue, such as by manipulation of a handpiece and/or by clamping tissue between the blade and a clamp member, the mechanical vibratory energy of the blade is transmitted to the tissue, not only cutting the tissue but also generating frictional heat and causing cavitation, coaptation and coagulation of the tissue.

In some instances, the blade is straight and, when used with a longitudinally vibrating transducer, vibrates solely in the longitudinal direction (parallel to the longitudinal axis of the waveguide). However, it is often desirable to provide ultrasonically driven blades that are curved in one or more directions. Curved blades provide a variety of advantages, including greater access to certain sites within a patient as well as improved visibility during use. While curved blades, when operatively connected to a longitudinally vibrating transducer (e.g., via an elongate waveguide) will generally vibrate in at least one non-longitudinal direction (e.g., transversely) due to the asymmetrical nature of the curved blade with respect to the longitudinal axis of the waveguide, such non-longitudinal vibrations in the blade during use can be advantageous. For example, some curved blades that vibrate in at least one non-longitudinal direction may provide greater blade displacement, particularly at the distal end of the blade.

It is also desirable in some instances to provide an ultrasonic surgical blade having a hook-shaped blade for use in, for example, dissecting tissue. Such blades typically have a single, hook-shaped blade along one side of the blade. One such hooked blade is shown and described in U.S. Pat. No. 5,324,299 ("the '299 Patent"), issued Jun. 28, 1994 and incorporated by reference herein. As discussed in the '299 Patent, such hooked blades are useful for cutting loose, unsupported tissue since the hook-shaped blade is able to grasp and tension the loose tissue, thereby cutting and coagulating the tissue. The hook portion is only provided on one side of the blade, and the remainder of the blade is flat, thereby limiting the usefulness of the blade.

Furthermore, curved or hooked blades can be difficult to manufacture. For example, curved blades of the prior art typically have one or more faces (i.e., surfaces) which are curved in two or more directions, thus requiring the use of specialized equipment such as angled chamfer end mills (also referred to as milling cutters), multiple types of end mills and precise depth-of-cut (Z-axis) control of the milling machine in order to obtain precise blade (i.e., "end effector") geometry. While simpler straight, non-hooked blades are easier to fabricate, allowing the use of less complex machining processes, these blades do not provide the benefits of a curved and/or hooked blade geometry.

While a variety of devices and techniques may exist for providing curved ultrasonically driven blades, it is believed that no one prior to the inventor has made or used an invention as described herein.

BRIEF DESCRIPTION OF THE DRAWINGS

While the specification concludes with claims particularly pointing out and distinctly claiming the invention, it is believed that the invention will be better understood from the detailed description of certain embodiments thereof when read in conjunction with the accompanying drawings. Unless the context indicates otherwise, like numerals are used in the drawings to identify similar elements in the drawings. In addition, some of the figures may have been simplified by the omission of certain elements in order to more clearly show other elements. Such omissions are not necessarily indicative of the presence or absence of particular elements in any of the exemplary embodiments, except as may be explicitly stated in the corresponding detailed description.

FIG. 8 depicts an end view of the embodiment shown in FIG. 5.

FIG. 9 depicts a bottom plan view of the embodiment shown in FIG. 5.

FIG. 10 depicts a top plan view of the embodiment shown in FIG. 5.

Figure 1:
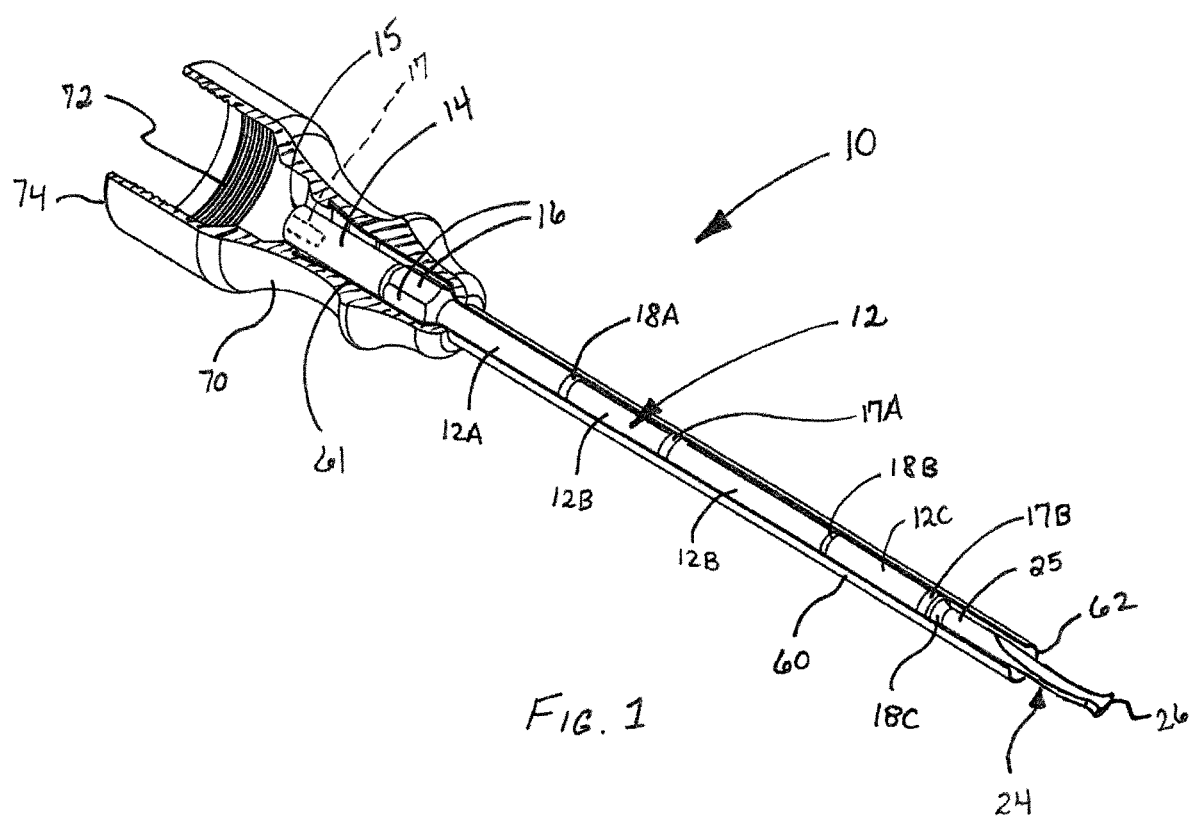
FIG. 1 depicts a partial cross-sectional view of one embodiment of an ultrasonic surgical device having a double hook curved blade.

The drawings are intended to illustrate rather than limit the scope of the present invention. Embodiments of the present invention may be carried out in ways not necessarily depicted in the drawings. Thus, the drawings are intended to merely aid in the explanation of the invention. Thus, the present invention is not limited to the precise arrangements shown in the drawings.

DETAILED DESCRIPTION

The following detailed description describes examples of embodiments of the invention solely for the purpose of enabling one of ordinary skill in the relevant art to make and use the invention. As such, the detailed description and illustration of these embodiments are purely illustrative in nature and are in no way intended to limit the scope of the invention, or its protection, in any manner. It should also be understood that the drawings are not to scale and in certain instances details have been omitted, which are not necessary for an understanding of the present invention.

Embodiments of the present disclosure provide a double hook curved blade for use with an ultrasonic transducer for medical purposes. The blades described herein are not only curved, but also have concave hook portions located on opposite sides of the blade. The double hook curved blades described herein provide a plurality of edges suitable for cutting tissue, in some embodiments including cutting edges having angles that vary along the length of the cutting edge for facilitating cutting and coagulating tissue. The double hook curved blades are provided at the distal end of a waveguide, and have a curved portion that extends lengthwise along at least a portion of the length of the blade and concave hook portions located on opposite sides of the curved portion of the blade. In some embodiments, the curved portion of the blade is provided by a pair of opposing first and second faces of the blade that are flat across their widths and curved along at least a portion of their respective lengths. In some instances, a clamp member is operatively located adjacent to the curved blade for selective engagement with a face of the blade so as to provide for both coagulating and cutting, thus providing a surgical forceps arrangement (also referred to as ultrasonic shears). With or without an associated clamp member, the cutting blade may be used for ultrasonically cutting, coagulating and/or dissecting tissue.

The double hook curved blade embodiments described herein are configured so as to simplify fabrication, while still providing a plurality of blade edges suitable for cutting tissue. By providing a plurality of blade edges, including variably angled edges, embodiments described herein allow surgeons to employ a greater range of techniques and effects. In addition, curved blade embodiments described herein also allow for tissue cutting in more than one direction, often without the surgeon having to reposition the device.

FIG. 1 is a partially cross-sectional view of one embodiment of an ultrasonic surgical device (10) comprising an elongate waveguide (12) and a double hook curved blade (24). In the particular embodiment shown, ultrasonic surgical device (10) also includes a sheath assembly comprising a hollow cylindrical sheath (60) and a sheath coupler (70) at the proximal end of the sheath (60). In other embodiments, the sheath assembly is omitted.

In the embodiment shown in FIG. 1, the waveguide (12) is located within the sheath (60) and sheath coupler (70). However, the sheath assembly is not secured directly to the waveguide (12). Instead, and as detailed below, waveguide (12) is operatively attachable at its proximal end to an ultrasonic transducer, and sheath coupler (70) is secured to the transducer housing. It will be understood, however, that waveguide (12) may be secured to the sheath assembly (i.e., to sheath (60) and/or sheath coupler (70)), such as by welding, adhesive attachment or in other ways known in the art.

The waveguide (12) includes an internally threaded connector portion (14) at its proximal end, as well as a plurality of flats (16) arrayed about the circumference of the waveguide (12) adjacent to connector portion (14). The flats (16) provide an integral nut on waveguide (12) for use in tightening the waveguide onto a transducer, as explained below. While waveguide (12) is depicted as being of unitary construction, in alternative embodiments waveguide (12) comprises two or more portions joined to one another (e.g., by threaded attachment). For example, in one alternative embodiment, connector portion (14) and flats (16) comprise a unitary structure which is threadably attached at the proximal end of waveguide (12) (e.g., by use of an internally threaded bore and a mating threaded stud connecting the two portions of the waveguide (12)). Similarly, although blade (24) is depicted as being integral with waveguide (12), in alternative embodiments the blade (24) is a separate structure that is attached to the distal end of waveguide (12), such as by threaded attachment.

Figure 2:
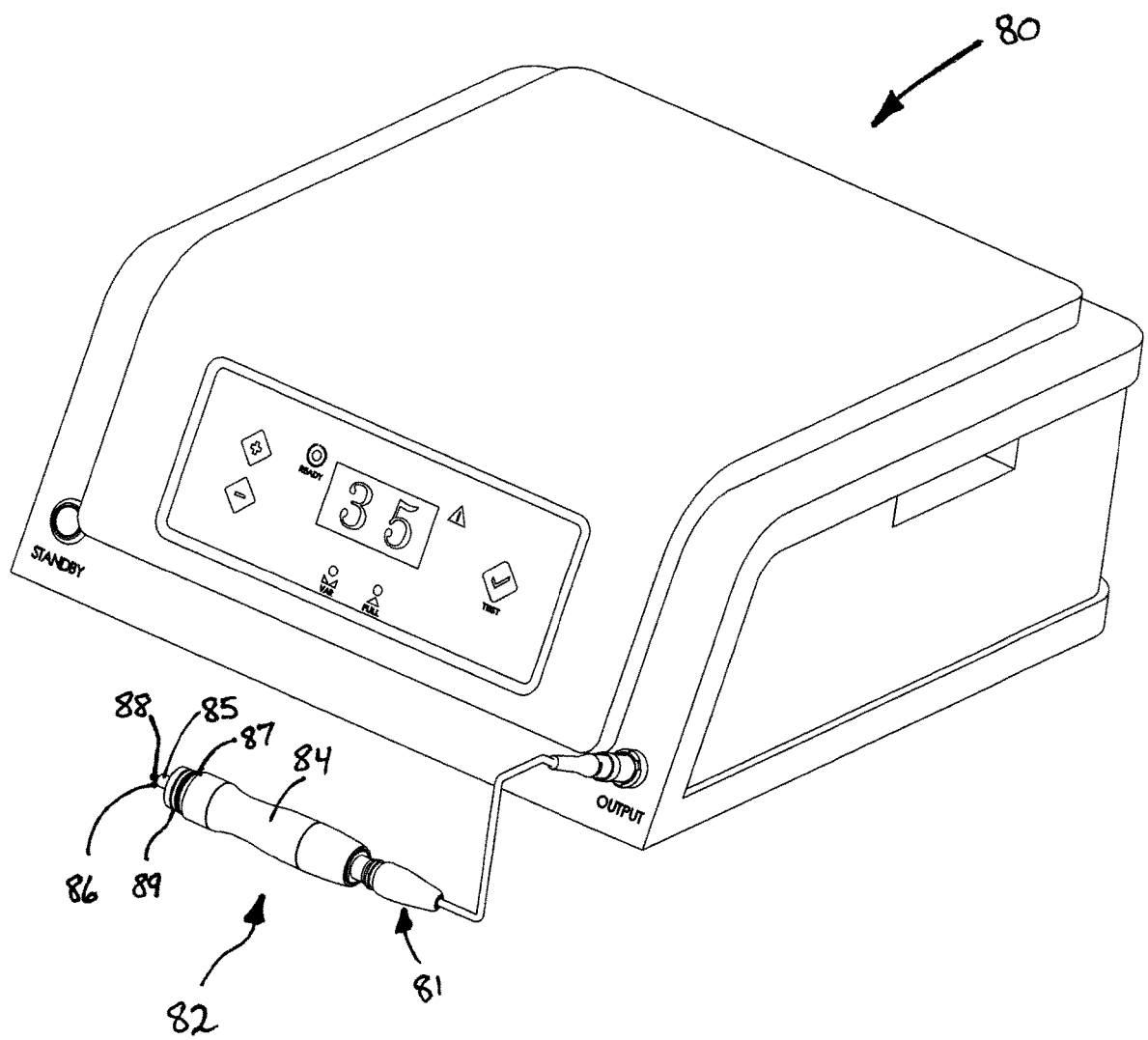
FIG. 2 depicts one embodiment of an ultrasonic generator and attached transducer with which the ultrasonic surgical device of FIG. 1 can be used.

FIG. 2 illustrates an exemplary generator (80) and ultrasonic transducer (82) with which the ultrasonic surgical device (10) may be used. It will be understood that generator (80) and transducer (82) are merely exemplary, as ultrasonic surgical device (10) can be used with any of a variety of generators and transducers. Transducer (82) includes a housing (84) which is configured to facilitate grasping and manipulation of the transducer housing (84) by a medical practitioner. The proximal end of the housing (84) includes an electrical connector (e.g., a plug or a socket) for operative connection to the generator (80) via a mating connector (81) provided at the end of a cable similarly connected to the generator (80). Thus, an electrical drive signal comprising an alternating current of ultrasonic frequency is supplied from the generator (80) to the transducer (82) via the cable and connector (81). Transducer (82) converts the drive signal into a standing, ultrasonic vibrational wave in the transducer, including the distal portion (85) of the transducer horn (or velocity transformer, not shown) which protrudes from the distal end of housing (84). The transducer housing (84) also includes a threaded projection (89) at its distal end, adjacent distal portion (85) of the transducer horn.

A threaded mounting stud (88) is secured to the distal portion (85) of the transducer horn, such as by being threadably and adhesively secured within a threaded bore (not shown) in distal portion (85). Thus, threaded stud (88) extends distally away from the distal end wall (86) of distal portion (85). It should also be pointed out that the distal end wall (86) of distal portion (85) of the transducer horn is located at an antinode of the standing vibrational wave produced by the transducer (82). By way of example, generator (80) and transducer (82) in the depicted embodiment are configured to generate a standing vibrational wave having a frequency of about 55 kHz. However, various other ultrasonic frequencies may be employed, such as between about 20 and about 120 kHz.

Ultrasonic surgical device (10) may be operatively coupled to the transducer (82) in a variety of ways. In the embodiment shown, connector portion (14) at the proximal end of the waveguide (12) includes a threaded bore (17) that extends inwardly (i.e., distally) from the proximal end wall (15) of connector portion (14). Threaded bore (17) is sized and configured to threadably receive mounting stud (88) of transducer (82) therein for operatively coupling the waveguide (12) to the transducer (82). When connector portion (14) is threaded onto the mounting stud (88) of the transducer (82), the proximal end wall (15) of connector portion (14) is in abutment with the distal end wall (86) of distal portion (85) of transducer (82). When coupled in this manner, the standing vibrational wave produced in the transducer is propagated along the length of the waveguide (12). Flats (16) are used to further tighten the waveguide (12) onto the distal end of the transducer (82), and a torque wrench (not shown) may be used to ensure that the waveguide is not over tightened.

As mentioned previously, the sheath assembly comprises cylindrical sheath (60) and sheath coupler (70), which are affixed to one another as shown. The sheath (60) may be affixed to the sheath coupler (70) in a variety of ways such as by welding, adhesive and/or swaging. In the exemplary embodiment shown in FIG. 1, a proximal portion (61) of sheath (60) is secured within a suitably configured cavity within coupler (70), adjacent the distal end of the coupler. Also, the inner diameter of proximal portion (61) of sheath (60) is larger than the inner diameter of the portion of sheath (60) external to the coupler (70) in order to receive the connector portion (14) and flats (16) of waveguide (12) within proximal portion (61).

Sheath coupler (70) is generally hollow and includes a threaded cavity (72) extending inwardly away from proximal end wall (74) of the coupler (70). Once the waveguide (12) has been operatively coupled to the transducer (82) in the manner described previously, the sheath assembly is slid over the waveguide (12). In particular, blade (24) is inserted through the threaded cavity (72) followed by waveguide (12). Thereafter, sheath coupler (70) is threadably secured to the transducer housing (84) by the threaded engagement of threaded projection (89) within threaded cavity (72), with the proximal end wall (74) of the coupler (70) in abutment with the end wall (87) of transducer housing (84). Once assembled in this manner, at least a portion of blade (24) extends beyond the distal end wall (62) of sheath (60), as seen in FIG. 1. In other words, in some embodiments, a proximal portion of the blade (including proximal portions of the first and second opposed faces, described further herein) is positioned within the sheath, while a distal portion of the blade extends beyond the distal end wall of the sheath (as depicted in FIG. 1). Of course, it will be understood that the waveguide (12), blade (24), and/or sheath assembly can be configured such that either more or less of the blade (24) extends beyond the distal end (62) of sheath (60) than is depicted in FIG. 1 (see, e.g., FIGS. 19A and 19B). In general, enough of blade (24) should protrude beyond the distal end of sheath (60) to provide adequate visualization, reach, and manipulation of the blade for cutting, dissection and coagulation during use, while not having so much of the blade (24) exposed that there is a heightened risk of unintended contact between the blade (24) and tissue.

In the embodiment shown in FIG. 1, between about 0.5 and about 2.5 cm of blade (24) extends beyond the distal end wall (62) of sheath (60). In other embodiments, between about 1.0 and about 2.0 cm of blade (24) extends beyond the distal end wall (62) of sheath (60). In still further embodiments, about 15% to about 85% of the distal ¼ wave, or about 30% to about 70% of the distal ¼ wave of the blade (24) is exposed. The distal ¼ wave is the region extending between the most distal vibrational node and the distal tip (26) of the blade—i.e., approximately the length of the blade (24) which extends from approximately the most distal node to the distal tip (26).

During use of the ultrasonic surgical devices and blades described herein, various forces applied at the blade (24) will tend to cause lateral deflection of the waveguide (12) within the sheath (60). In order to prevent contact between the inner wall of sheath (60) and blade (24) and waveguide (12), thereby limiting or preventing potential damage to the ultrasonic device (10) as well as damping of the standing wave, one or more spacers are provided between the waveguide (12) and the interior of sheath (60) in order to maintain the waveguide (12) in the center of the sheath (60) (i.e., the longitudinal axis of the waveguide (12) aligned with the longitudinal axis of the sheath (60)). In the embodiment shown in FIG. 1, resilient rings (17A, 17B) are provided on the exterior of waveguide (12), and comprise, for example, silicone rings. Since the amplitude of the longitudinal vibration of the waveguide (12) at the driving frequency (e.g., 55 kHz) during use is zero at the nodes of the standing wave, the resilient rings (17A, 17B) are located at or near the vibrational nodes of the waveguide (12) in order to limit damping of the standing wave. Rings (17A, 17B) also damp any vibrations having frequencies other than the drive frequency, since the nodes of vibrations of other frequencies will generally not coincide with the node locations for the drive frequency.

Resilient rings (17A, 17B) can be supported and maintained in place in a variety of ways known to those skilled in the art. For example, annular supports for the resilient ring can be provided on the waveguide, and the resilient ring can be, for example, insert molded over the support or secured over the annular support in other ways known to those skilled in the art (e.g., adhesively, bonding, etc.). Annular supports can be formed, for example, by lathe turning. As yet another alternative, circumferential grooves can be provided on the waveguide (e.g., by lathe turning so as to form two adjacent rings with the groove located therebetween). The resilient ring can then be maintained in position mechanically by trapping the ring within the groove. In some embodiments, resilient rings (17A, 17B) are provided at or near two or more vibrational nodes, depending in part on the length of the waveguide.

As is known to those skilled in the art, a variety of other features may be provided on the waveguide (12). For example, waveguide (12) shown in FIG. 1 includes a plurality of segments of varying diameter, with tapers (18A, 18B, 18C) providing a smooth transition between segments of different diameters. In the exemplary embodiment shown in FIG. 1, first segment (12A) is located adjacent flats (16) and has a diameter smaller than that of the flats (16) region in order to amplify the standing vibrational wave. A first taper (18A) is located at the distal end of first segment (12A), and provides a smooth transition from the larger diameter of first segment (12A) to the smaller diameter of second segment (12B). Similarly, a second taper (18B) is located at the distal end of second segment (12B), and provides a smooth transition from the smaller diameter of second segment (12B) to the larger diameter of third segment (12C). Finally, a third taper (18C) is located at the distal end of third segment (12C) (adjacent resilient ring (17B), at the most-distal vibrational node of the waveguide), and provides a smooth transition from the larger diameter of third segment (12C) of waveguide (12) to the smaller diameter of the blade (24). These changes in diameter serve to, among other things, adjust the amplitude and/or frequency of the vibrational wave propagating the length of the waveguide. It will be understood, however, that this is merely one exemplary arrangement of the waveguide. Alternative embodiments include any number of segments of varying diameters, depending, in part, on the desired length of the waveguide (which will depend, for example, on the intended use of the instrument).

Figure 3:
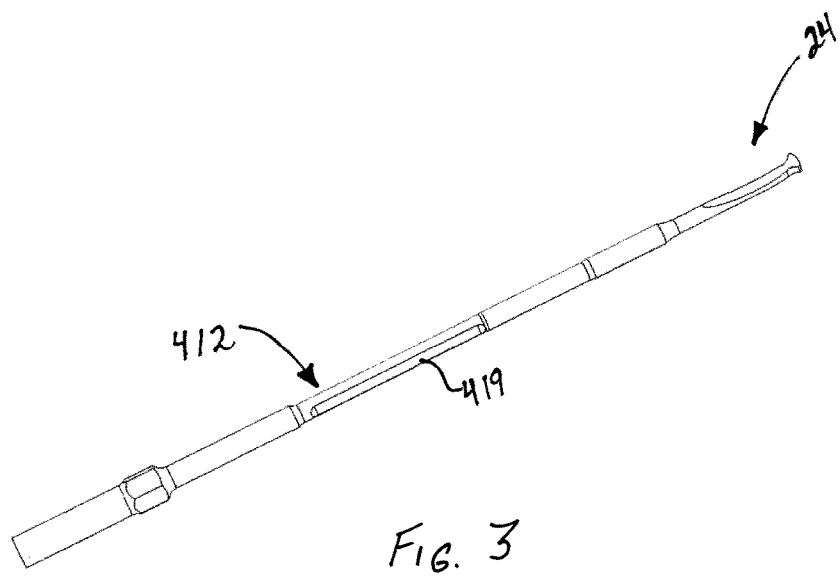
FIG. 3 depicts a perspective view of a modified version of the ultrasonic surgical device of FIG. 1, wherein the waveguide has been modified from that depicted in FIG. 1.
Figure 4:
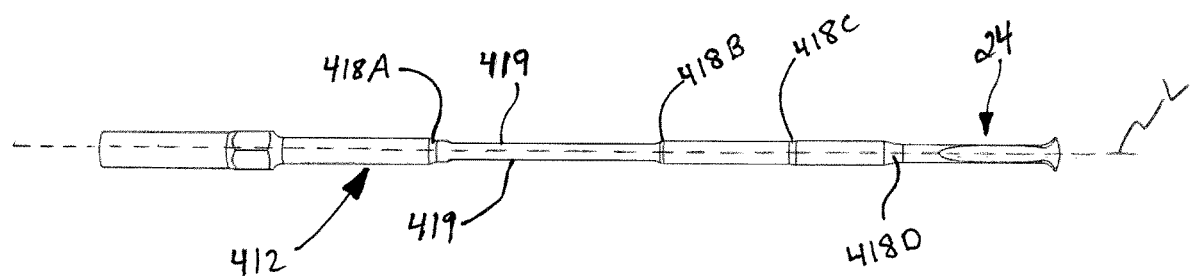
FIG. 4 depicts top plan view of the waveguide and blade of FIG. 3.

In the modified version of the waveguide (412) shown in FIGS. 3 and 4, four tapers (418A-418D) are provided on the waveguide (412). In addition, a pair of flats (419) are provided on opposite sides of the waveguide (e.g., by milling). As is known to those skilled in the art, flats (419) are used to damp any vibrations having frequencies other than the drive frequency (also referred to as parasitic vibrations).

The ultrasonic surgical device comprising waveguide (12) and blade (24) can be made from any of a variety of materials, particularly various medically and surgically acceptable metals such as titanium, titanium alloy (e.g., Ti6Al4V), aluminum, aluminum alloy, or stainless steel. The waveguide (12) and blade (24) shown in FIG. 1 are formed as a single unit, fabricated from a single metal rod that has been milled so as to provide the depicted features. Alternately, the waveguide and blade may comprise two or more separable components of the same of differing compositions, with the components coupled to one another by, for example, adhesive, welding, a threaded stud, and/or other suitable ways known to those skilled in the art. For example, waveguide (12) may be configured as two pieces joined together at or between flats (16) and first segment (12A). Similarly, blade (24) may be constructed separately from waveguide (12) and joined to the distal end of waveguide (12).

It will also be understood that the ultrasonic surgical device comprising waveguide (12) and blade (24) may be used without the sheath assembly simply by operatively coupling the proximal end of the waveguide (12) (i.e., connector portion (14)) to transducer (82) (via threaded mounting stud (89)). Sheath (60), however, not only protects the waveguide (12), but also prevents inadvertent contact between the waveguide (12) and the patient, medical personnel or the surgical environment. Not only will such contact damp vibration of the waveguide (12), but it can also cause injury to the patient or medical personnel since the waveguide (12) is ultrasonically vibrating.

As mentioned previously, the blades depicted and described herein are not only curved, but also have concave hook portions located on opposite sides of the blade. The double hook curved blades described herein provide a plurality of edges suitable for cutting tissue, including varying edge angles for facilitating cutting and coagulating tissue. These blades can be fabricated from round stock using only simple lathe turning and end mills, with no Z-axis milling, while still providing a plurality of blade edges suitable for cutting tissue.

Figure 5:
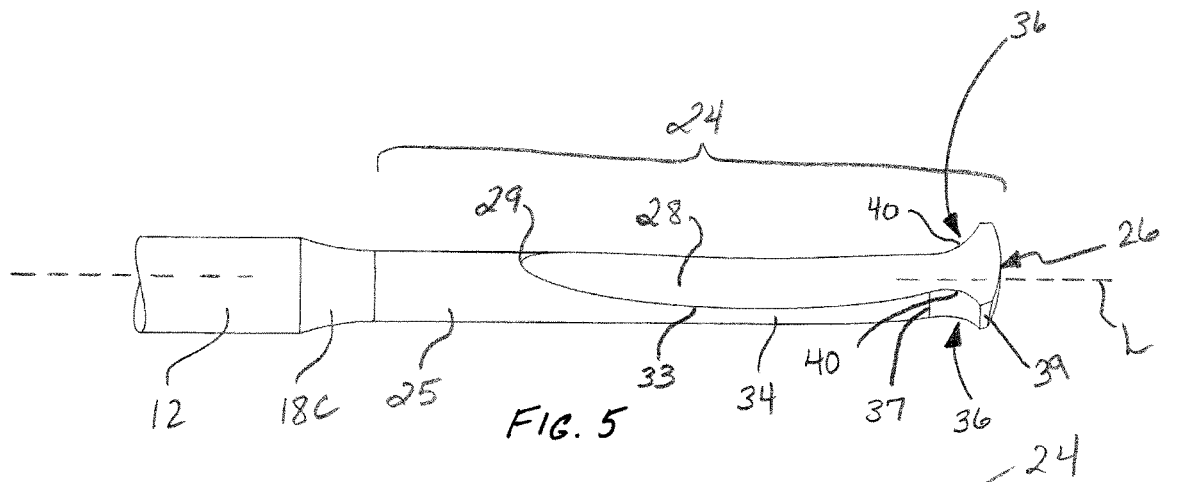
FIG. 5 depicts a top perspective view of the blade and a portion of the waveguide of the ultrasonic surgical device of FIG. 1.

The double hook curved blades depicted and described herein are provided at the distal end of a waveguide, and have a curved portion that extends lengthwise along at least a portion of the length of the blade and concave hook portions located on opposite sides of the curved portion of the blade. In some embodiments, the curved portion of the blade is provided by a pair of opposing first and second faces of the blade that are flat across their widths, which width extends perpendicular to the projected longitudinal axis (L) of the waveguide (see FIG. 4). Along their respective lengths (i.e., the direction orthogonal to their respective widths), each of the first and second curved faces includes one or more curved segments, with each of the curved segments of an individual face being curved in the same direction (however, that curvature can be positive and/or negative curvature). In these embodiments, the direction of curvature of the curved segments of the first and second opposed faces does not change along their respective lengths, with the curvature gradient on the surface of each face being non-zero in one direction (for the curved segments of each face) and zero in the perpendicular direction (i.e., across their widths). Thus, the axes of curvature of each of the curved segments of an individual face are parallel to one another (as seen, for example, in FIG. 5). In addition, the axes of curvature of each of the curved segments of the faces of the blade is perpendicular to a plane which includes the longitudinal axis (L) of the waveguide (i.e., the faces of the blade include no curved segment having an axis of curvature which is not perpendicular to a plane which includes the longitudinal axis of the waveguide).

Accordingly, in those embodiments wherein the curved portion of the blade is provided by a pair of opposing first and second faces of the blade that are flat across their widths and curved along their lengths in a single direction, the first and second faces comprise developable surfaces, thereby facilitating the manufacture of the blade from round stock using an end mill and only X- and Y-axis movement of the workpiece (i.e., the blade material, e.g., round stock) and mill with respect to one another. No Z-axis movement or cutting is required during milling the first and second faces, since each is flat and/or includes one or more right cylindrical surfaces (circular or elliptic cylindrical surfaces). (The configuration of the blade faces described by the foregoing may be better understood with references to the method of producing the blade faces from round stock, as further described herein.)

The first and second opposing faces are spaced apart from one another along their lengths, with the blade having sidewalls comprising cylindrical surfaces extending between the first and second faces along either side of the blade. As used herein, unless the context indicates otherwise, the term cylindrical surface includes not only a portion of the surface of a right circular cylinder, but also a portion of the surface of a tapered or elliptical cylinder (e.g., the blades described herein can be fabricated from any turned stock, including not only straight or tapered cylindrical stock but also straight or tapered elliptical turned stock).

The intersections between each of the first and second faces and each of the sidewalls define blunt cutting edges, which extend along at least a portion of the length of the blade (e.g., a portion of the length of the first and second opposed faces of the blade). Because each of the first and second blade faces is not necessarily curved in the same manner, a variety of cutting edge shapes and configurations can be provided on the same blade in order to give more cutting options to the medical practitioner.

Figure 6:
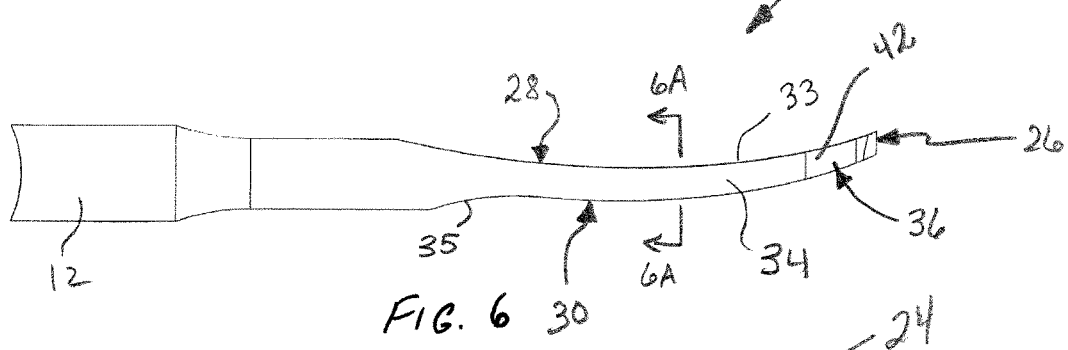
FIG. 6 depicts a side view of the embodiment shown in FIG. 5.
Figure 7:
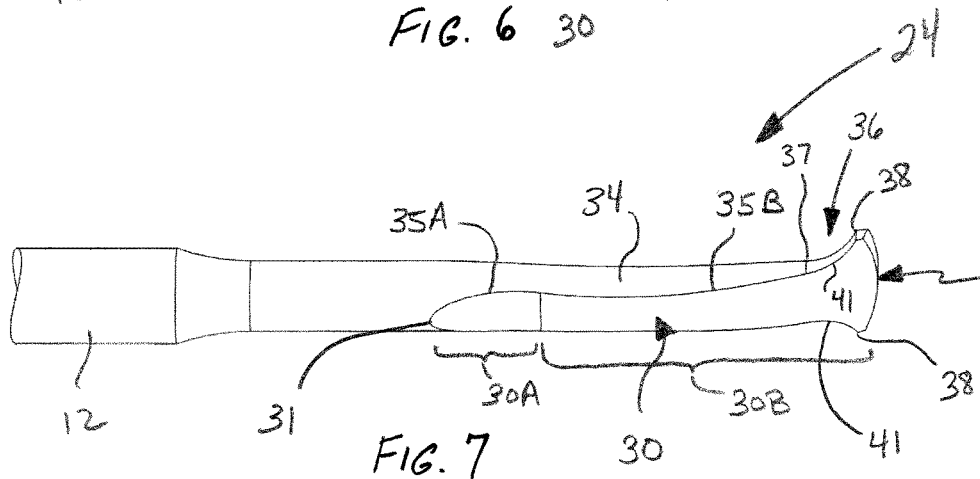
FIG. 7 depicts a bottom perspective view of the embodiment shown in FIG. 5.
Figure 6A:
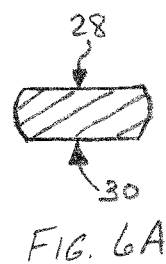
FIG. 6A depicts a cross-sectional view of a portion of the blade shown in FIG. 6, taken along the line 6A-6A thereof.

Furthermore, in embodiments further described herein and depicted in the figures, the axes of curvature for the curved portions of the first and second faces are parallel to one another—i.e., the first and second faces curve in the same direction (although that direction of curvature can be positive or negative on different portions of each face). This is best seen, for example, in FIG. 11 which depicts a side plan view of blade (24) (the same view as FIG. 6), which shows the curvatures of the first and second blade faces. As a result, even though the blade may taper in thickness along portions of its length, the cross-sectional shape of the blade in any plane perpendicular to the longitudinal axis of the waveguide through the first and second faces of the blade is as depicted in FIG. 6A. This cross-sectional shape, similar to a stadium or discorectangle, comprises four sides—a pair of flat, parallel sides (i.e., the opposing first and second faces), and a pair of opposed curved sides (i.e., the cylindrical surface sidewalls). It will be understood, however, that since the curvature of the first and second faces is not necessarily the same throughout the blade (i.e., the blade can be tapered), the flat, parallel sides of a cross-section through the first and second faces of the blade are not necessarily of the same width. This can be seen, for example, in FIG. 6A wherein the first, or upper face 28 is wider than the second, or lower face 30. FIGS. 9 and 10 also depict how the widths of the first and second faces (28, 30) are not identical to one another at every point along the length of the blade, as well as not having a constant width along their respective lengths.

The concave hook portions located on opposite sides of the blade can extend inwardly into the cylindrical surface sidewalls of the blade, formed, for example, by advancing a rotating end mill into each sidewall of the blade. When formed in this manner, the cross-sectional shape of the blade in any plane perpendicular to the longitudinal axis of the waveguide through the hook portions may comprise, for example, a rectangle or a trapezoid (if hook portions are cut at an angle).

Alternatively, and as further described below, in some embodiments each of the concave portions comprises a portion of an outwardly curved (i.e., concave) surface of revolution, such as a portion of the surface of a circular hyperboloid (i.e., a "hyperboloidal surface") extending between the first and second faces of the blade, wherein the axis of the surface of revolution coincides with the longitudinal axis (L) of the waveguide. In this instance, the cross-sectional shape of the blade in any plane perpendicular to the longitudinal axis of the waveguide through the hook portions will be the same as that shown in FIG. 6A, with the flat, parallel sides of the cross-section not necessarily of the same width. In fact, when the first and second faces (28, 30) have different widths (as shown in FIGS. 9 and 10), the angle between the first face (28) and the interior surface (42) of each hook portion will be different than the angle between the second face (30) and the interior surface (42) of the hook portions. This feature provides different angles for the cutting edge at the intersection of each hook portion and the first face and the cutting edge at the intersection of each hook portion and the second face. As noted below, this arrangement wherein the hook portions comprise hyperboloidal surfaces (or portions of other outwardly curved surfaces of revolution) also facilitates the fabrication of the blade from round stock using simple lathe turning to provide the hyperboloidal surface and end mills to produce the first and second faces of the blade.

In addition, because the hook portions are identical to one another and are located on opposite sides of the blade, the blade embodiment depicted in the drawings is also symmetrical with respect to a plane that includes the longitudinal axis (L) of the waveguide (i.e., a plane orthogonal to the plane of FIGS. 9 and 10). Because of this as well as the curvature of the blade, the blade will vibrate both longitudinally and transversely (i.e., in the X- and Y-directions of FIG. 17, but not in the Z-direction).

Turning to the specific embodiment of a blade (24) depicted in FIGS. 5-11, the proximal end of the blade (24) (i.e., the portion of the blade adjacent the waveguide (12)) comprises a cylindrical portion (25) located between the distal end of the waveguide (12) and the curved portion of the blade. Cylindrical portion (25) is thus located between the taper (18C) (typically adjacent the most-distal node of the waveguide) and the proximal ends of first and second faces (28, 30) (also referred to herein as the upper and lower faces, respectively). In alternative embodiments, no such cylindrical portion is included on the proximal end of the blade.

Figure 11:
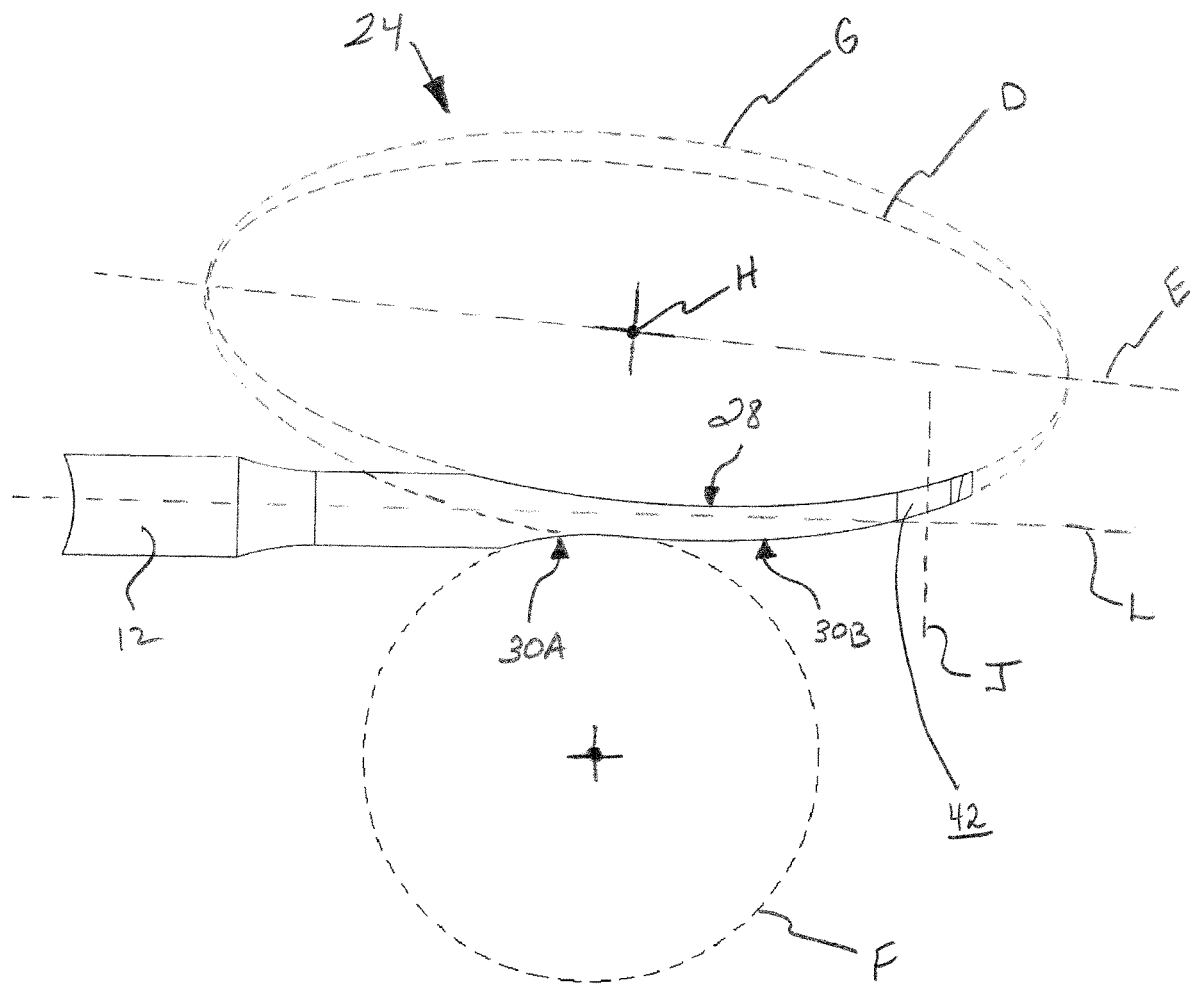
FIG. 11 depicts a schematic illustration of the curvature of the first and second faces of the blade shown in FIG. 6.

First and second opposed faces (28, 30) are located on opposite sides of the blade (24), extending distally away from cylindrical portion (25) to distal tip (26). In this particular embodiment, first (or upper) face (28) is flat across its width and curved (in a single direction) along its length, wherein its width is defined as extending perpendicular to the projected longitudinal axis (L) of the waveguide (see FIG. 5) and its length extends orthogonal to its width (i.e., parallel to the longitudinal axis (L)). In the embodiment shown, first face (28) is continuously curved along its entire length, having a positive, elliptical curvature (as best seen in FIG. 11). As used herein, the axis of curvature of an elliptically curved surface, such as first and second faces (28, 30) whose curvature is defined by an ellipse (D, G) in FIG. 11, is defined as a line extending through center point (H) parallel to the width of the first and second faces and perpendicular to the longitudinal axis (L). The axis of rotation of other complex curves can be similarly defined. As also used herein, a concave surface has a positive curvature, while a convex surface such as the distal segment (30B) of second face (30) has a negative radius of curvature.

Along its length, the curvature of first face (28) follows a portion of an ellipse (D) that is tilted with respect to the longitudinal axis (L) of the waveguide (12). Thus, as seen in FIG. 11, the major axis (E) of ellipse (D) is not parallel to the longitudinal axis (L), but rather is tilted at an included angle of about 5 degrees. Of course the elliptical path of first face (28) need not be tilted with respect to the longitudinal axis (L) or may be tilted to varying degrees (e.g., up to about 20 degrees, or between about 2 and about 10 degrees). It will also be understood that first and second faces (28, 30) can be curved in any of a variety of manners, such as having a single, uniform radius of curvature (i.e., a surface that follows a portion of a circular path), a constantly varying radius of curvature along its entire length (or a portion thereof), or segments of varying curved shapes and/or curvature including one more segments that are flat across both their width and length. However, in the depicted embodiments, the direction of curvature of the first and second opposed faces does not change along their respective lengths, such that the axes of curvature of each of the curved portions of the first and second faces are parallel to one another (as seen, for example, in FIG. 11). In addition, the axes of curvature of each of the curved portions of the first and second faces (28, 30) of the blade are perpendicular to a plane which includes the longitudinal axis (L) of the waveguide (i.e., the faces of the blade include no curved portion having an axis of curvature which is not perpendicular to a plane which includes the longitudinal axis of the waveguide).

Second (or lower) face (30) is also flat across its width and curved (in a single direction) along its length. In the depicted embodiment, however, second face (30) includes a positively curved (concave) transition segment (30A) and a negatively curved (convex) distal segment (30B). Transition segment (30A) provides a smooth transition from cylindrical portion (25) to the distal segment (30B) of the curved portion of the blade. Not only is transition segment (30A) of second face (30) necessitated by the use of an end mill to form the blade faces in turned stock, the transition segment (30A) helps to reduce stress at the intersection of the second face (30) and the cylindrical portion (25). Nevertheless, the transition segment (30A) as well as the edges (35A) between transition segment (30A) and the cylindrical surface sidewalls (34) extending between the first and second faces (28, 30) are also usable portions of the blade. Thus, for example, edges (35A), like edges (35B) between distal segment (30B) and sidewalls (34), can be used for cutting and/or cauterizing tissue.

Transition segment (30A) as well as distal segment (30B) of second face (30) are flat across their widths and curve in a single direction along the length of second face (30). In the embodiment shown, the curvature of transition segment (30A) follows a portion of a circle (F) (see FIG. 11). Once again, however, the axis of curvature of transition segment (30A) (i.e., the center of circle (F)) is parallel to the axes of curvature of first face (28) (i.e., the foci of ellipse (D)), and is perpendicular to a plane which includes the longitudinal axis (L) of the waveguide. The curvature of distal segment (30B), on the other hand, is not only negative (i.e., distal segment (30B) is convex), it follows a portion of an ellipse (G) that, like ellipse (D), is tilted with respect to the longitudinal axis (L) of the waveguide (12). In fact, although merely exemplary of one embodiment, ellipses D and G are concentric (i.e., have a common center point (H) and major and minor axes). However, since the eccentricity of ellipse (G) is less than that of ellipse (D), the distance between first face (28) and second face (30) decreases along their lengths such that the blade (24) is slightly tapered. It will be understood, of course, that a variety of other curvatures (e.g., a non-tilted ellipse) may be used for the curvature of one or both of the first and second faces (28, 30), as desired.

It should be noted that, although the first and second faces (28, 30) are flat across their respective widths, these surfaces appear to be slightly curved across their widths in the end view of FIG. 8. However, this apparent curvature in FIG. 8 is simply the result of distal end (26) being curved (further described below), combined with the longitudinal curvature of the first and second faces (28, 30). In an alternative embodiment, distal end (26) is flat (see, e.g., FIG. 14), and in such an embodiment an end view like that of FIG. 8 would not appear to show widthwise curvature of the first and second blade faces.

As mentioned previously, the first and second opposing faces (28, 30) are spaced apart from one another along their lengths by cylindrical surface sidewalls (34) extending between the first and second faces along either side of the blade (24) between the proximal ends (29, 31) of the first and second faces (28, 30) and the proximal ends (37) of the concave hook portions (36) located adjacent the distal end (26) of blade (24). The intersections between each of the first and second faces (28, 30) and the sidewalls (34) define blunt cutting edges (33, 35) that extend along at least a portion of the length of the blade. Due to, for example, the tilting of, and eccentricity differences between, ellipses D and G and the resulting differences in curvature of the first and second faces (28, 30), as well as the fact that one face is concave and the other convex, the bluntness (i.e., angle) of the cutting edges (33, 35) vary independently along their respective lengths. This aspect of blade (24), as well as other embodiments of such double hook curved blades, provide a plurality of cutting options to the medical practitioner in order to meet the needs of a particular medical procedure and/or patient. For example, different cutting and/or coagulating properties can be obtained simply by rotating or otherwise moving the position of the blade so as to employ any of the variety of cutting edges, edge angles and surfaces provided by the blade (24).

Concave hook portions (36) are located adjacent the distal end (26) of blade (24), on opposing sides of the blade. The concave hook portions (36) extend between the first and second faces (28, 30), flaring outwardly from the sidewalls (34) along the length of the hook portions. Thus, the proximal ends (37) of the hook portions (36) generally have the same diameter, and even the same circumferential curvature, as the distal end of sidewalls (34). Although the distal end (38) of hook portions (36) can extend to the distal end (26) of the blade (24), in the embodiment shown the distal end (38) is spaced slightly from distal end (26) such that a pair of surfaces (39) are located between the distal ends (38) of hook portions (36) and the distal end (26) of the blade. In the depicted embodiments, surfaces (39) comprise cylindrical surfaces similar to, but greater in diameter than sidewalls (34) and cylindrical portion (25) at the proximal end of the blade (see, e.g., FIGS. 9 and 10).

Each of the concave hook portions (36) comprises a portion of an outwardly curved (i.e., concave) surface of revolution, such as a portion of the surface of a circular hyperboloid (i.e., a "hyperboloidal surface"), extending between the first and second faces (28, 30) of the blade. The axis of rotation of the outwardly curved surface of revolution coincides with (i.e., is the same as) the longitudinal axis (L) of the waveguide (12), as will be apparent from the description of how the hook portions (36) are fabricated. Thus, a pair of curved cutting edges (40) are provided along the intersection of first face (28) and the concave surface of revolution (e.g., a hyperboloidal surface) of each hook portion (36). Likewise, a pair of curved cutting edges (41) are provided along the intersection of second face (30) and the concave surface of revolution of each hook portion (36).

As will be apparent, each of the curved cutting edges (40, 41) not only curves in the same direction of curvature of the first and second faces (28, 30) (e.g., elliptically upward when viewed from the side), but also curves outwardly away from the longitudinal axis of the waveguide. For example, when concave hook portions comprise portions of a circular hyperboloid, the curved cutting edges curve about an axis (J) (see FIG. 11) that is orthogonal to both the longitudinal axis (L) as well as the axes of curvature of the first and second faces (28, 30). (Technically, the axis J is a focal point of the hyperbola whose surface of revolution defines the hyperboloidal surface of the hook portions.) Furthermore, since the interior surface (42) of each hook portion (36) comprises a hyperboloidal surface (or other concavely curved surface of revolution) with an axis of revolution coinciding with the longitudinal axis (L) of the waveguide (12), the interior surface (42) of each hook portion (36) is curved about the longitudinal axis (L). As a result, the cutting edges defined by the intersection of the first and second faces (28, 30) with the hook portions (i.e., interior surface (42)) not only curves and varies in angle along their respective lengths, the upper hook cutting edges (40) (i.e., the intersection of the first face (28) with the hook portions) are not identical to the lower hook cutting edges (41). For example, the angle of the upper hook cutting edge (40) at any given point along the length of the hook portion of the blade can be different from the angle of the lower hook cutting edge (41). In the example shown, since the second face (30) is wider than the first face (28) throughout the length of the hook portion of the blade, the angle of the lower hook cutting edge (41) is smaller than the angle of the upper hook cutting edge (40) (i.e., the lower hook cutting edge (41) is sharper). Nevertheless, as explained below, the blade (24), including concave hook portions (36), is readily fabricated from turned stock using simple lathe turning to provide the hyperboloidal surface (or other concavely curved surface of revolution) and end mills to produce the first and second faces of the blade.

Figure 14:
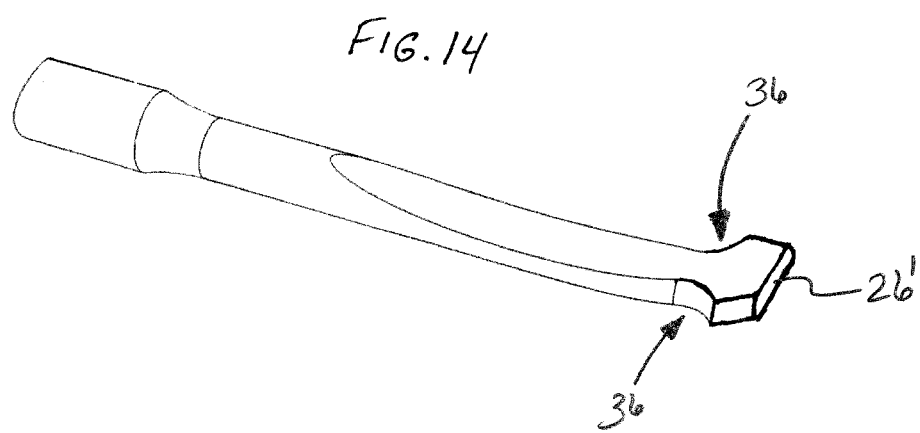

The distal end (26') of the blade (24) can be flat, as shown in FIG. 14, or curved as shown in FIGS. 3-10 and 15. Curved distal end (26) provides additional cutting and coagulating properties and options for the surgeon, as do cylindrical surfaces (39) between the distal end (38) of the hook portions (36) and the distal end (26) of the blade.

Figure 16:
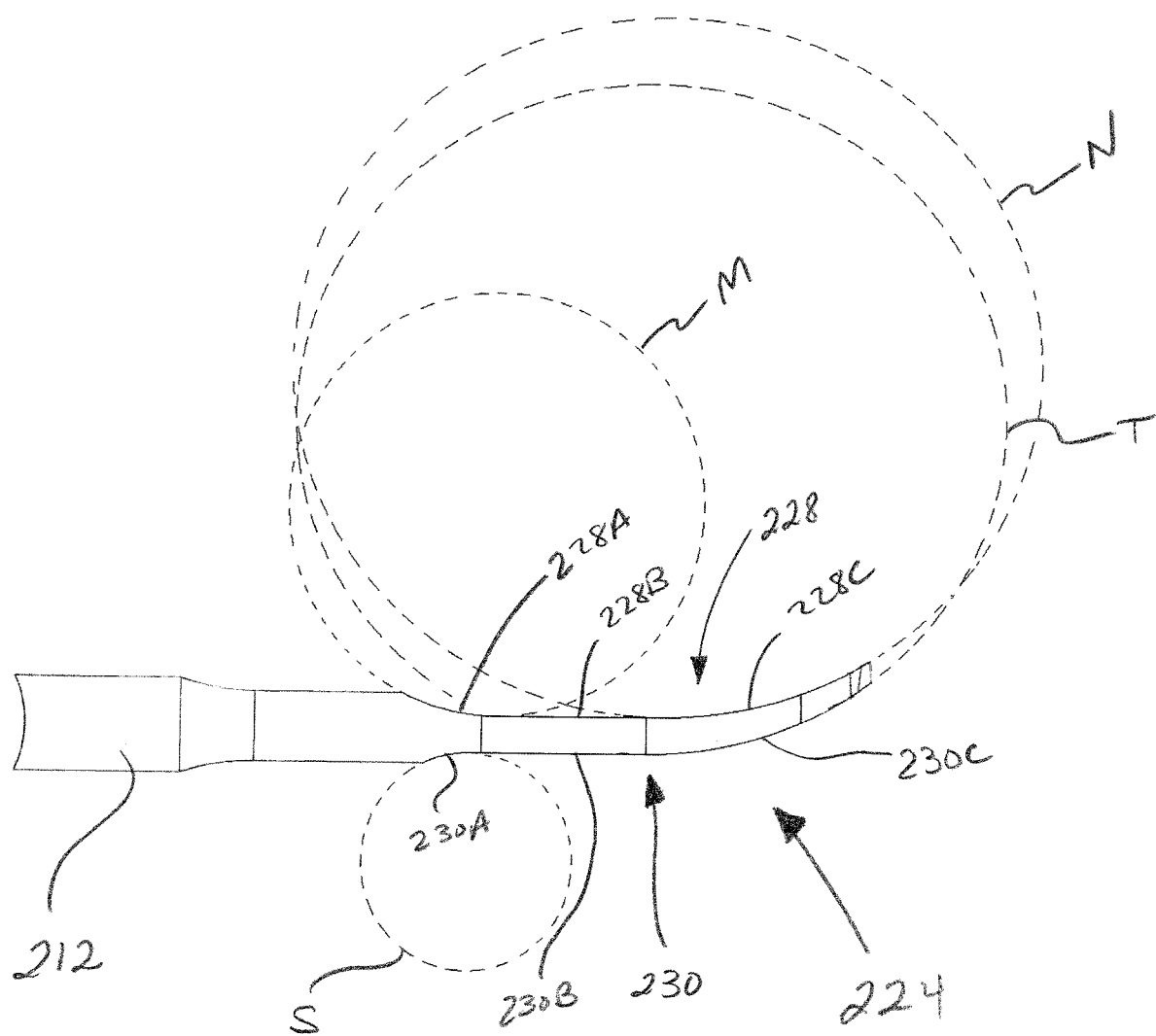
FIG. 16 depicts a schematic illustration of the curvature of the first and second faces of an alternative embodiment of a double hook curved blade.

As mentioned previously, in alternative embodiments the opposed first and second faces of the blade can have segments of varying amounts of curvature, but still with the axes of curvature for the curved segments parallel to one another—i.e., the first and second faces curve in the same direction (although that direction of curvature can be positive or negative on different portions of each face). Such an alternative embodiment is depicted in FIG. 16, wherein blade (224) has first and second faces (228, 230), each having a plurality of segments of varying curvature (but all of the curved segments curving in the same direction, and flat across their widths).

Thus, first face (228) includes a proximal (or transition) segment (228A) concavely curved about a portion of a first circle (M), an intermediate flat segment (228B) having no curvature, and a distal segment (228C) concavely curved about a portion of a second circle (N) having a larger radius than the first circle (M). Similarly, second face (230) includes a proximal (or transition) segment (230A) (similar to transition segment (30A) that is concavely curved about a portion of a third circle (S), an intermediate flat segment (228B) having no curvature, and a distal segment (228C) convexly curved about a portion of a fourth circle (T) having a larger radius than the third circle (S). The hook portions of blade (224) are similar to hook portions (36) of the previously described embodiment. It will be understood that any number of segments can be provided on the first and second faces of the double hook curved blades, some of which can be flat (either parallel or tapered with respect to the longitudinal axis of the waveguide), while others are curved (e.g., about a portion of a circle or ellipse). In general, at least one segment of each of the first and second faces is curved (i.e., has a non-zero curvature gradient), in particular at least the distal most segments of each of the first and second faces (i.e., the portion of the first and second faces immediately adjacent to the hook portions of the blade).

In addition, in most embodiments the second face has a concavely curved transition segment extending distally away from the proximal end of the second face, and a convexly curved distal segment extending proximally away from the distal end of the second face. The first face in these embodiments, on the other hand, has only concavely curved or flat segments, such as a continuous curvature along its entire length (e.g., first face (30)) or at least a concavely curved distal segment extending proximally away from the distal end of the first face.

FIGS. 12-15 depict a method of manufacturing blade (24) from a segment (44) of round stock, wherein only a portion of waveguide (12) is shown for purposes of clarity. Starting from a single round stock (e.g., a cylindrical rod), the omitted features of waveguide (12) (e.g., tapers (18)) are formed by methods known to those skilled in the art. In particular, the diameter of the originally round stock has been reduced in FIG. 12 to provide not only taper (18C), but also a cylindrical section (46) having a radius corresponding to not only the desired radius of cylindrical portion (25) but also the cylindrical surface sidewalls (34). Taper (18C) and cylindrical section (46) can be formed, for example, by turning the original round stock on a lathe to reduce its diameter. Similarly, a hyperboloidal surface (48) (or other concavely curved surface of revolution) is formed adjacent the distal end of the segment (44) of round stock, optionally leaving distal cylinder (50) at the distal end of the turned stock having the same diameter as (or less than) the diameter of the original round stock. Hyperboloidal surface (48) (technically speaking, one-half of a hyperboloid of one sheet) provides the interior surfaces (42) of each hook portion (36). Distal cylinder (50) provides the pair of surfaces (39) located between the distal ends (38) of hook portions (36) and the distal end (26) of the blade.

Figure 12:
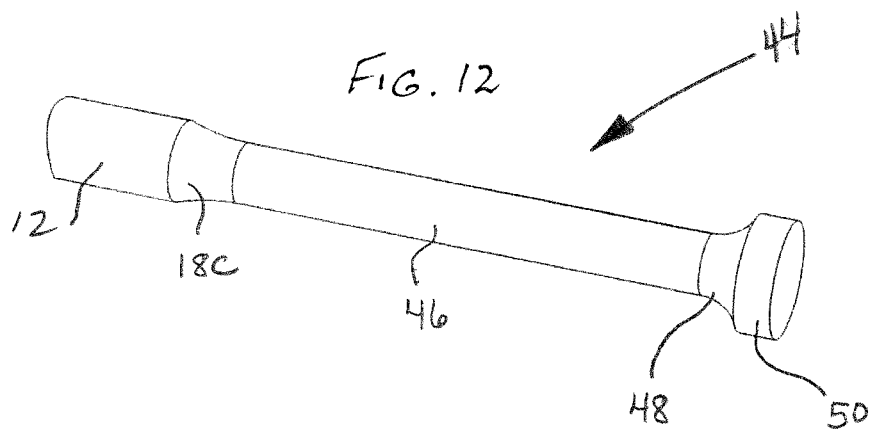
FIGS. 12-15, 17 and 18 depict a method of manufacturing the blade portion of the embodiment of FIG. 5.
Figure 13:
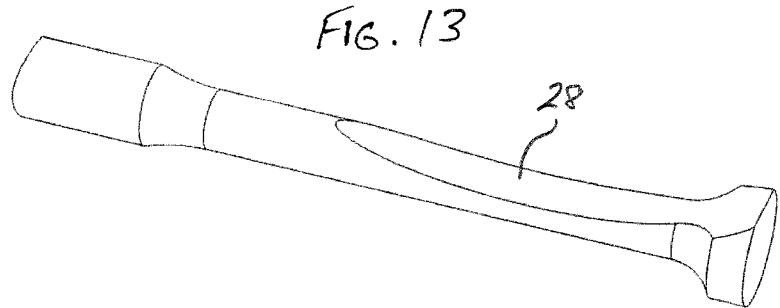
Figure 17:
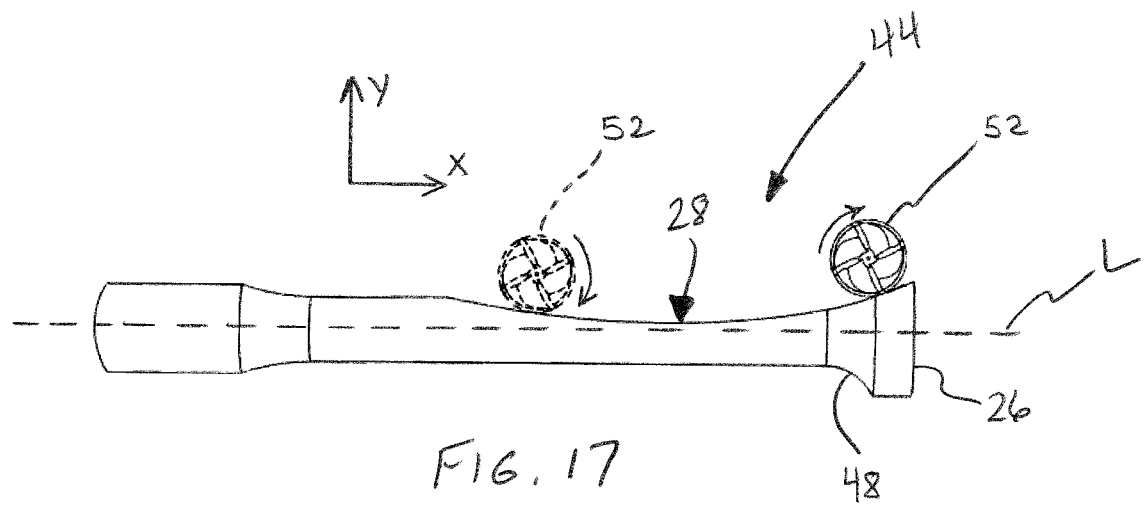
Figure 18:
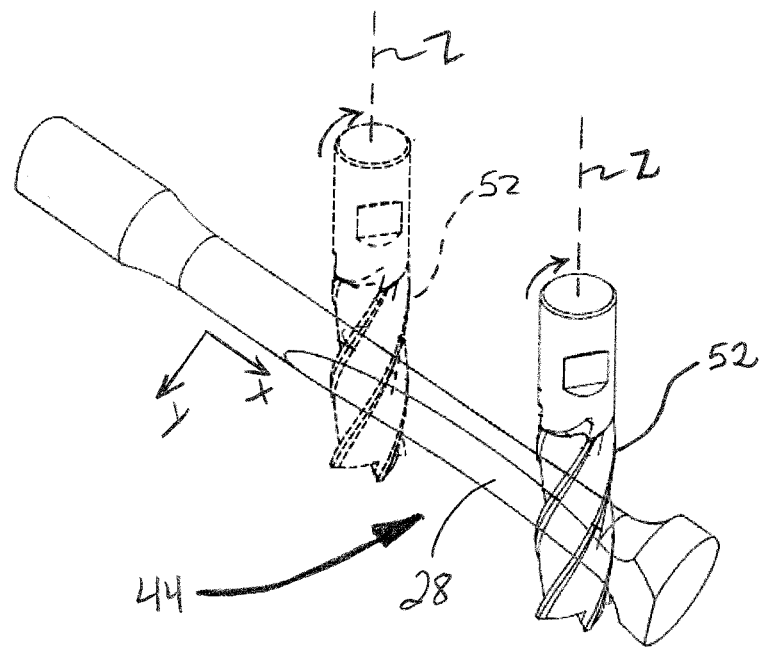

Following size reduction of the round stock to the configuration shown in FIG. 12, the first face (28) of the blade (24) is machined using an end mill to produce the configuration shown in FIG. 13. However, no Z-axis milling is required. For example, first face (28) is milled into the turned stock using an end mill (52) as shown in FIGS. 17 and 18. The workpiece (the turned stock (44)) is positioned on the X-Y table of a milling machine, as shown in FIGS. 17 and 18. The workpiece is then advanced in the X- and Y-directions, without rotation of the workpiece, as the end mill is spinning (about a Z-oriented axis). As a result, first face (28) is milled into the workpiece, wherein first face (28) is flat across its width (i.e., the Z-direction in FIG. 18). Second face (30) is milled in the same manner, without the need to rotate the workpiece about its longitudinal axis (L) but rather merely moving the workpiece in the Y-direction for reorientation prior to milling second face (30) to produce the partially completed blade shown in FIG. 14. (Alternatively, the workpiece may be rotated 180 degrees about its longitudinal axis from the position shown in FIG. 18 in order to machine (mill) second face (30).)

Figure 15:
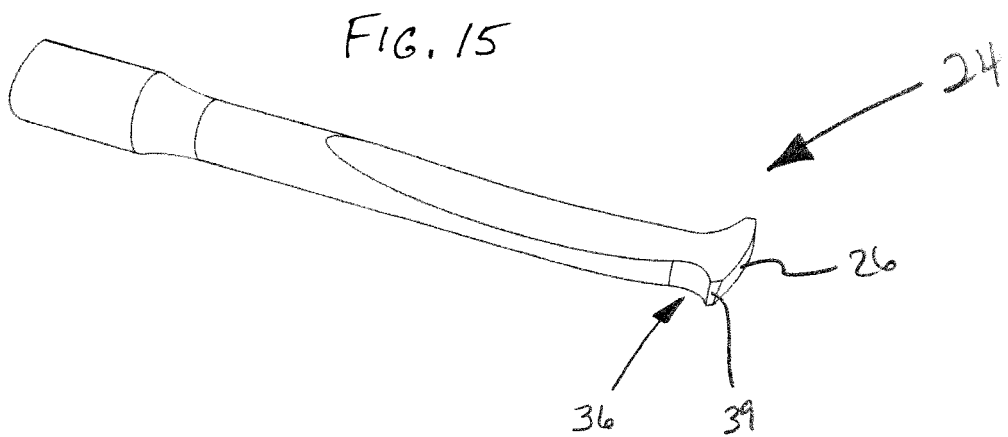

As a result of milling first and second faces (28, 30) using end mills, hook portions (36) are provided on the blade (24), corresponding to portions of hyperboloidal surface (48) (or other concavely curved surface of revolution). While the blade (24) may be used in the form shown in FIG. 14, in the depicted embodiment the distal end (26) of the blade is milled such that the distal end (26) is curved (as shown in FIG. 15). In other words, the distal end (26) of the blade is rounded off.

Figure 19A:
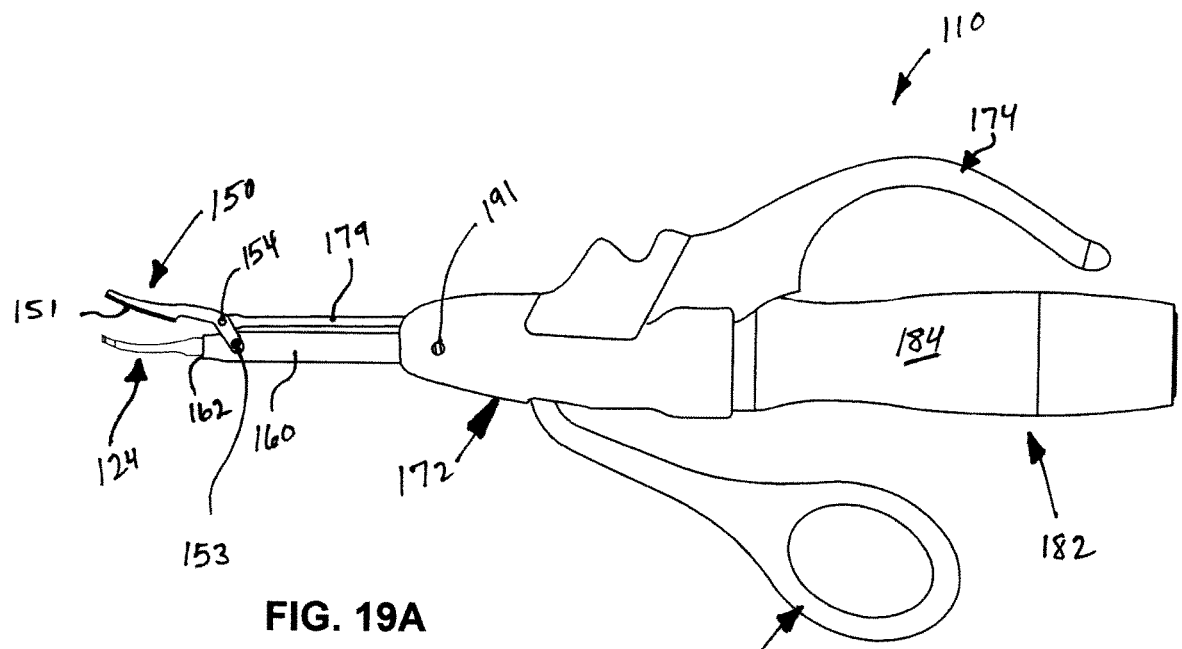
FIG. 19A depicts a schematic side view of an ultrasonic shears device.
Figure 19B:
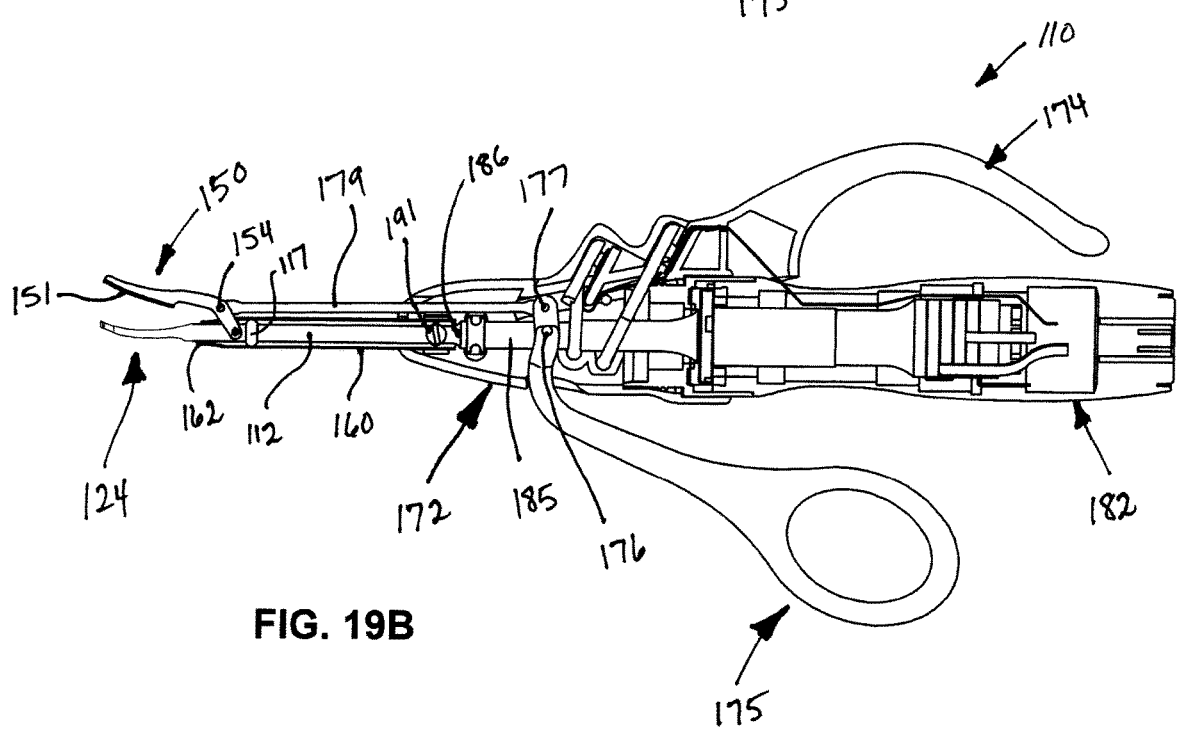
FIG. 19B depicts a partial cross-sectional view of the ultrasonic shears device of FIG. 19A.

An alternative embodiment of an ultrasonic surgical device (110) is depicted in FIGS. 19A and 19B, wherein the device (110) is configured as ultrasonic shears (also known as a clamp coagulator or ultrasonic forceps) having a clamp member (150) pivotally supported adjacent blade (124), wherein blade (124) is similar to the double hook curved blades (24, 224) described previously herein. The clamp member (150) is adapted for selective engagement with a face of the blade (124) so as to provide for the simultaneous cutting and coagulation of tissue urged against the face of blade (124) by the clamp member (150). In the embodiment shown, clamp member (150) is located and configured for selective engagement with the first (or upper) face of the blade (124).

Ultrasonic surgical device (110) is, apart from the blade (124) and the clamp member (150), similar to the apparatus shown and described in U.S. Pat. No. 5,322,055 (which is incorporated by reference herein). Like the previous embodiment, the curved blade (124) is provided at the distal end of an elongate waveguide (112). While waveguide (112) and blade (124) are depicted as being of unitary construction, in alternative embodiments waveguide (112) comprises two or more portions joined to one another (e.g., by threaded attachment). Similarly, although blade (124) is depicted as being integral with waveguide (112), in alternative embodiments the blade (124) is of separate structure and attached to the distal end of waveguide (112), such as by threaded attachment. Ultrasonic surgical device (110) also includes a hollow cylindrical sheath (160) in which at least a portion of waveguide (112) and optionally a portion of blade (124) is positioned.

As in the previous embodiment, although at least a portion of the waveguide (112) is located within the sheath (160), the sheath (160) is not secured directly to the waveguide (12). Instead, and as detailed below, waveguide (112) is operatively attached at its proximal end to a transducer (182), and the proximal end of sheath (160) is secured within the handpiece (172).

Ultrasonic surgical device (110) further includes an ultrasonic transducer (182) mounted to the handpiece (172), as shown. Transducer (182) may be removably mounted to the handpiece (172), such as by threaded engagement therewith, or may be fixed within or on the handpiece (172). Transducer (182) includes a housing (184) which is configured to facilitate grasping and manipulation of the surgical device (110) along with stationary handle (174) of handpiece (172). The proximal end of the transducer housing (184) includes an electrical connector (e.g., a plug or a socket) for operative connection to a generator. Thus, an electrical drive signal comprising an alternating current of ultrasonic frequency will be supplied from the generator to the transducer (182) via a cable operatively connected to the electrical connector on the transducer housing. As with the previous embodiment, transducer (182) converts the drive signal into a standing, ultrasonic vibrational wave in the transducer, including the transducer horn (or velocity transformer) (185).

Although not shown in FIG. 19A or 19B, a threaded mounting stud is secured to the distal end (186) of the transducer horn (185), such as by being threadably and adhesively secured within a threaded bore in the distal end (186) of the transducer horn (185). Thus, as in the previous embodiment, this threaded stud extends distally away from the distal end (186) of transducer horn (185), and this distal end (186) of transducer horn (185) is located at an antinode of the standing vibrational wave produced by the transducer (182) (e.g., at 55 kHz). Similar to the previous embodiment, the proximal end of waveguide (112) includes a threaded bore (not shown) that extends inwardly (i.e., distally) from the proximal end of the waveguide (112). This threaded bore is sized and configured to threadably receive the mounting stud on the distal end of the transducer horn (185), such that the waveguide (112) is operatively coupled to the transducer (182) by threadably securing the waveguide onto the mounting stud of the transducer horn (185). When coupled in this manner (i.e., as seen in FIG. 19B), the standing vibrational wave produced in the transducer (182) is propagated along the length of the waveguide (112).

The sheath (160) may be affixed to the handpiece (172) in a variety of ways known to those skilled in the art, such as by welding, adhesive, mechanical fasteners and/or swaging. In the exemplary embodiment shown in FIGS. 19A and 19B, the proximal end of sheath (160) and the waveguide (112) are secured within handpiece (172) by a mounting pin (191).

As seen in FIG. 19A, at least a portion of blade (124) extends beyond the distal end wall (162) of sheath (160). Once again it will be understood that the waveguide (112), blade (124), sheath (160) and/or handpiece (172) can be configured such that more or less of the blade extends beyond the distal end of sheath (160) than depicted in FIG. 19A. In this instance, the entirety of the first and second blade faces (i.e., the curved portion of the blade) extends beyond the distal end wall (162) of sheath (160). As with the previously described embodiment, one or more resilient rings (117) are provided on the exterior of waveguide (112) (e.g., silicone rings) and act as spacers that not only maintain the waveguide (112) centered with sheath (160), but also are located at vibrational nodes of the waveguide (112) in order to limit damping of the standing wave at the drive frequency while also damping frequencies other than the drive frequency.

Clamp member (150) includes a pad (151) mounted thereto for compressing tissue against a face or edge of the blade (124) in order to facilitate the cutting and coagulating of tissue. Pad (151) is formed of a polymeric or other compliant material, and engages the first face of the blade (124) when the clamp member (150) is pivoted to its fully closed position. Pad (151) can comprise, for example, PTFE or polyimide (PI), with or without added filler materials such as glass, metal and/or carbon. In some embodiments, pad (151) comprises a high temperature resistant material. Pad (151) is attached to the clamp member (150) by, for example, an adhesive or mechanical fastener. As seen in FIGS. 19A and 19B, the exposed surface of the pad (151) provides a curved tissue-engaging surface. In the embodiment shown, this tissue-engaging surface has a curvature corresponding to the curvature of the corresponding portion of the first face of the blade.

The proximal end of the clamp member (150) is pivotally mounted to the sheath (160), adjacent the distal end thereof, by a pivot pin (153). The clamp member (150) is also pivotally attached to the distal end of an actuator rod (179) at pivot pin (154). Actuator rod (179) is mounted to the handpiece (172) for linear movement parallel to the longitudinal axis of waveguide (112), and extends outwardly from the handpiece (172) directly above the sheath (160). From the open position of FIG. 19A, linear movement of the actuator rod (179) in the distal direction (i.e., towards blade (124)), causes the clamp arm to pivot towards its closed position, such that pad (151) will eventually engage the first face of the blade (124). Similarly, from the closed position, linear movement of the actuator rod (179) in the proximal direction (i.e., towards transducer (182)), causes the clamp arm to pivot to its open position of FIG. 19A.

In order to effect linear, longitudinal movement of actuator rod (179), a pivoting handle (175) is pivotally mounted to handpiece (172), as shown. Handle (175) is pivotally secured within handpiece (172) at pivot pin (176), and the distal end of handle (175) is pivotally attached to the proximal end of actuator rod (179) at pivot pin (177) within handpiece (172). Thus pivotal movement of handle (175) away from handpiece (172) causes the clamp member (150) to pivot towards its open position (FIG. 19A), while pivotal movement of handle (175) towards handpiece (172) causes the clamp member (150) to pivot towards its closed, tissue clamping, position.

While various embodiments of ultrasonic surgical devices and blades thereof have been described in detail above, it will be understood that the components, features and configurations, as well as the methods of manufacturing the devices and methods described herein are not limited to the specific embodiments described herein.

What is claimed is:

1. An ultrasonic surgical device comprising:
   (a) an elongate waveguide having a longitudinal axis and a distal end; and
   (b) a blade extending away from the distal end of the waveguide, said blade having:
      a length,
      a distal end,
      first and second opposed faces extending lengthwise along at least a portion of the length of the blade, and sidewalls extending between the first and second faces along either side of the blade such that said first and second opposing faces are spaced apart from one another, wherein each of said first and second faces has a width that extends perpendicular to the longitudinal axis of the waveguide and a length that extends orthogonal to said width, and
      a pair of hook portions, said hook portions located on opposite sides of the blade, each hook portion having a continuous interior surface that extends between said first and second opposed faces;
   wherein each of said first and second opposed faces is flat across its width and includes one or more curved segments along its length, with each of the curved segments of an individual face being curved in the same direction such that the axes of curvature of each of the curved segments of an individual face are parallel to one another, and the axes of curvature of each of the curved segments of the faces of the blade are perpendicular to a plane which includes the longitudinal axis of the waveguide.

2. The ultrasonic surgical device of claim 1, wherein each of the curved segments of said first and second faces are curved in the same direction such that their axes of curvature of are parallel to one another.

3. The ultrasonic surgical device of claim 2, wherein the thickness of the blade is smallest at its distal end.

4. The ultrasonic surgical device of claim 1, wherein each of said hook portions has a concave interior surface that flares outwardly from one of said sidewalls in the distal direction.

5. The ultrasonic surgical device of claim 4, wherein the interior surface of each of said hook portions comprises a portion of a concavely curved surface of revolution extending between the first and second faces of the blade.

6. The ultrasonic surgical device of claim 5, wherein said concavely curved surface of revolution comprises a hyperboloidal surface having an axis of rotation that coincides with the longitudinal axis of the waveguide.

7. The ultrasonic surgical device of claim 4, wherein said hook portions are located adjacent the distal end of the blade.

8. The ultrasonic surgical device of claim 4, wherein the intersections between each of the first and second faces and the interior surface of each of said hook portions define cutting edges that curve in two directions.

9. The ultrasonic surgical device of claim 8, wherein, in one or more planes perpendicular to the longitudinal axis of the waveguide, the angle of the cutting edges defined by the intersections between the first face and the interior surface of each of said hook portions is larger than the angle of the cutting edges defined by the intersections between the second face and the interior surface of each of said hook portions.

10. The ultrasonic surgical device of claim 1, wherein said sidewalls comprise cylindrical surfaces extending between the first and second faces.

11. The ultrasonic surgical device of claim 10, wherein the intersections between each of the first and second faces and each of the sidewalls define cutting edges, and further wherein the angles of said cutting edges defined by the intersections between each of the first and second faces and each of the sidewalls vary along at least a portion of the length of the cutting edges.

12. The ultrasonic surgical device of claim 1, wherein said first face comprises at least one curved segment having a positive curvature.

13. The ultrasonic surgical device of claim 12, wherein said first face is continuously and positively curved along its entire length.

14. The ultrasonic surgical device of claim 12, wherein said second face comprises at least one curved segment having a negative curvature.

15. The ultrasonic surgical device of claim 14, wherein said second face further comprises a curved transition segment having a positive curvature, said transition segment located proximal to the curved segment of the second face having a negative curvature.

16. The ultrasonic surgical device of claim 1, wherein said first face comprises at least one curved segment having a positive elliptical curvature.

17. The ultrasonic surgical device of claim 16, wherein said elliptical curvature follows a portion of an ellipse that is tilted with respect to the longitudinal axis of the waveguide.

18. The ultrasonic surgical device of claim 12, wherein said second face comprises at least one curved segment having a negative elliptical curvature.

19. The ultrasonic surgical device of claim 1, wherein said first face comprises an elliptically curved segment having a positive elliptical curvature and extending to the distal end of the blade, and said second face comprises an elliptically curved segment having a negative elliptical curvature and extending to the distal end of the blade, wherein said elliptically curved segments of the first and second faces each follow portions of ellipses that are concentric with one another.

20. The ultrasonic surgical device of claim 1, wherein the interior surface of each of said hook portions comprises a portion of a surface of revolution extending between the first and second faces of the blade, with the axis of rotation of each of said surfaces of revolution coinciding with the longitudinal axis of the waveguide.

21. The ultrasonic surgical device of claim 20, wherein each of said hook portions has a concave interior surface which flares outwardly in the distal direction from a distal end of one of said sidewalls.

22. The ultrasonic surgical device of claim 21, wherein each of said hook portions are located adjacent the distal end of the blade.

23. The ultrasonic surgical device of claim 20, wherein said first face comprises an elliptically curved segment having a positive elliptical curvature and extending to the distal end of the blade, and said second face comprises an elliptically curved segment having a negative elliptical curvature and extending to the distal end of the blade.

24. The ultrasonic surgical device of claim 20, wherein said waveguide and said blade are integrally formed as a unitary structure from a metal chosen from the group consisting of titanium, titanium alloy, aluminum, aluminum alloy, and stainless steel.

25. The ultrasonic surgical device of claim 20, further comprising a clamp member having a curved tissue-engaging surface, said clamp member pivotally supported adjacent the blade, wherein said tissue-engaging surface has a curvature corresponding to the curvature of at least a portion of said first face of the blade, and further wherein the claim member is selectively pivotable between an open position whereat the clamp member is spaced away from the blade and a closed position whereat the clamp member can urge tissue against said first face of the blade.

26. A method of fabricating the ultrasonic surgical device of claim 1 from a segment of round stock without Z-axis milling, comprising the steps of:
  (a) turning a segment of round stock to form an outwardly curved surface of revolution adjacent a distal end of said segment of round stock; and
  (b) milling said round stock using an end mill in order to produce said first and second opposed faces;
wherein said first and second opposed faces extend from the distal end of said segment of round stock through and proximally beyond said outwardly curved surface of revolution, and said interior surfaces of said hook portions comprise the remaining portions of said surface of revolution.

* * * * *